United States Patent
Sharma et al.

(10) Patent No.: US 10,495,578 B2
(45) Date of Patent: *Dec. 3, 2019

(54) METHODS AND SYSTEMS TO ANALYZE A GAS-MIXTURE (71) Applicant: General Electric Company, Schenectady, NY (US)

(72) Inventors: Rachit Sharma, Karnataka (IN); Chayan Mitra, Karnataka (IN); Vinayak Tilak, Karnataka (IN)

(73) Assignee: General Electric Company, Schenectady, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/106,409

(22) Filed: Aug. 21, 2018

(65) Prior Publication Data

US 2019/0086335 A1    Mar. 21, 2019

Related U.S. Application Data (63) Continuation of application No. 15/304,247, filed as application No. PCT/US2015/023968 on Apr. 2, 2015, now Pat. No. 10,094,781.

(30) Foreign Application Priority Data

Apr. 14, 2014    (IN) .......................... 1942/CHE/2014

(51) Int. Cl.
  *G01N 21/65*    (2006.01)
  *G01N 21/03*    (2006.01)
  *G01N 33/00*    (2006.01)

(52) U.S. Cl.
  CPC ............. *G01N 21/65* (2013.01); *G01N 21/03* (2013.01); *G01N 21/031* (2013.01);
  (Continued)

(58) Field of Classification Search
  CPC .................................................... G01N 21/031
  See application file for complete search history.

(56) References Cited

U.S. PATENT DOCUMENTS 3,825,325 A    7/1974  Hartley et al.
4,410,271 A    10/1983 Matthews
(Continued)

FOREIGN PATENT DOCUMENTS

| DE | 19615365 A1 | 10/1997 |
|----|-------------|---------|
| GB | 2256083 A   | 11/1992 |
| GB | 2259767 A   | 3/1993  |

OTHER PUBLICATIONS

Submann et al. "Frequency shifting of pulsed narrow-band laser light in a multipass Raman cell", Optics Communications, ScienceDirect, Apr. 1, 1992, pp. 408-414, vol. 88, Issues 4-6, Garching, Germany.
Lempert et al. "Stimulated Raman scattering and coherent anti-Stokes Raman spectroscopy in high-pressure oxygen", Journal of the optical society of America B, Optics Info Base, May 1, 1990, pp. 715-721, vol. 7, Issue 5.

(Continued)

*Primary Examiner* — Shawn Decenzo
(74) *Attorney, Agent, or Firm* — Mintz Levin Cohn Ferris Glovsky and Popeo, P.C.

(57) ABSTRACT

A system is presented. The system includes an electromagnetic radiation source configured to generate a mode matched electromagnetic radiation that irradiates a gas mixture filled in a gas compartment at a determined pressure 'P' bars, an intensity enhancement mechanism that internally reflects the mode-matched electromagnetic radiation a plurality of times to achieve an effective intensity 'E', of reflected electromagnetic radiation in a region of interest, that is 'N' times an intensity of the mode-matched electromagnetic radiation, and a detection subsystem that analyses the gas-mixture based upon Raman Scattered photons emitted from the region of interest, wherein a product of the 'P' and the 'N' is at least 30.

19 Claims, 4 Drawing Sheets

(52) U.S. Cl.
CPC ..... *G01N 33/0027* (2013.01); *G01N 21/0317* (2013.01); *G01N 2021/651* (2013.01); *G01N 2201/062* (2013.01); *G01N 2201/06113* (2013.01); *G01N 2201/12* (2013.01)

(56) References Cited

U.S. PATENT DOCUMENTS

| | | | |
|---|---|---|---|
| 4,648,714 A | | 3/1987 | Benner et al. |
| 4,953,976 A | * | 9/1990 | Adler-Golden ........ G01N 21/65 356/301 |
| 5,272,717 A | * | 12/1993 | Stultz ..................... H01S 3/305 359/327 |
| 5,293,395 A | | 3/1994 | Fournier et al. |
| 5,786,893 A | * | 7/1998 | Fink ....................... G01N 21/65 356/301 |
| 5,822,058 A | | 10/1998 | Adler-Golden et al. |
| 6,157,455 A | * | 12/2000 | Pinvidic ............. G01N 21/3504 250/343 |
| 6,555,820 B1 | | 4/2003 | Tacke et al. |
| 7,148,963 B2 | | 12/2006 | Owen et al. |
| 7,248,357 B2 | | 7/2007 | Servaites et al. |
| 7,446,317 B2 | | 11/2008 | Doyle |
| 7,595,882 B1 | | 9/2009 | Chen et al. |
| 7,764,379 B1 | | 7/2010 | McDermott |
| 8,073,637 B2 | | 12/2011 | Cline et al. |
| 8,363,216 B2 | | 1/2013 | Yuan et al. |
| 10,094,781 B2 | | 10/2018 | Sharma et al. |
| 2003/0081206 A1 | | 5/2003 | Doyle |
| 2009/0164138 A1 | * | 6/2009 | Goto ................. G01N 21/3504 702/24 |
| 2011/0211193 A1 | | 9/2011 | Saveliev et al. |
| 2011/0313670 A1 | | 12/2011 | De Greeve et al. |
| 2012/0176600 A1 | | 7/2012 | Falk et al. |
| 2012/0261578 A1 | | 10/2012 | Scott et al. |
| 2015/0131094 A1 | * | 5/2015 | Alquaity ................ G01J 3/42 356/326 |
| 2016/0153890 A1 | | 6/2016 | Scott |

OTHER PUBLICATIONS

Buric et al. "Raman Sensing of Fuel Gases Using a Reflective Coating Capillary Optical Fiber", Fiber Optic Sensors and Applications VI, SPIE, 2009, pp. 1-8, vol. 7316, 731608.

Buric PhD, Michael, "Gas Phase Raman Spectroscopy Using Hollow Waveguides", University of Pittsburgh, Swanson School of Engineering, 2010, pp. 1-199.

Kiefer et al. "Design and characterization of a Raman-scattering-based sensor system for temporally resolved gas analysis and its application in a gas turbine power plant; Raman sensor system for gas analysis", Measurement Science and Technology,IOP, Bristol, GV, vol. 19, No. 8, Aug. 1, 2008, p. 85408, XP020144354, ISSN: 0957-0233.

Kastner, Joachim, "Online Gas Quality Measurement Technique based on Optical and Thermal Gas Properties", Elster-Instromet Systems, Dec. 5-6, 2005, pp. 1-14, Chicago, IL.

Li, et al. "Diagnosis of Multiple Gases Separated from Transformer Oil Using Cavity-Enhanced Raman Spectroscopy", Chinese Physical Society and IOP Publishing Ltd., 2008, pp. 3326-3329, vol. 25, No. 9.

Kc, et al. "Improved multiple-pass Raman spectrometer", Applied Optics, Aug. 20, 2011, pp. 4805-4816, vol. 50, No. 24.

Goldstein et al. "Real-Time Optical BTU Measurement of Natural Gas at Line Pressure", 4th International Symposium of Fluid Flow Measurement, Jun. 27-30, 1999, pp. 1-13, Denver, Colorado.

Salter, et al. "Cavity-enhanced Raman spectroscopy with optical feedback cw diode lasers for gase phase analysis and spectroscopy", The Analyst, vol. 137, No. 20, Jan. 1, 2012, p. 4669, XP55200649, ISSN: 0003-2654.

Taylor, et al. Enhanced Raman sensitivity using an actively stabilized external resonator:, Review of Scientific Instruments, AIP, Melville, NY, US, vol. 72, No. 4 Apr. 1, 2001, pp. 1970-1976, XP012039069, ISSN: 0034-6748.

Buldakov et al. "Raman gas-analyzer for analyzing environmental and technogenic gas media", Atmospheric and Oceanic Optics Springer Germany, vol. 25, No. 4, Jul. 2012, pp. 298-303, XP55201109, ISSN: 1024-8560.

Elster-Instromet; Gas-lab Q1 EN03, Gas quality analyser, product brochure, Mar. 2010, 2 pages, Mainz-Kastel, Germany.

* cited by examiner

METHODS AND SYSTEMS TO ANALYZE A GAS-MIXTURE

CROSS-REFERENCE TO RELATED APPLICATIONS

This application is a continuation of U.S. patent application Ser. No. 15/304,247, entitled "METHODS AND SYSTEMS TO ANALYZE A GAS-MIXTURE," filed on Oct. 14, 2016, which is a national stage application, filed under 35 U.S.C. § 371, of International Application No. PCT/US2015/023968, filed on Apr. 2, 2015, and claims the benefit of, and priority to, IN Patent Application No. 1942/CHE/2014, filed on Apr. 14, 2014, each of which is incorporated by reference herein in its entirety.

BACKGROUND

Natural gas is generally a hydrocarbon gas mixture consisting primarily of methane, and includes varying amounts of other alkanes, carbon dioxide, nitrogen, hydrogen sulfide, and other rare gases. Accordingly, natural gas for commercial and industrial use comes in a wide array of compositions. Natural gas is an energy source and used in varied applications. For example, natural gas is used for heating, cooking, power generation, transportation, and has many other utilities. Additionally, natural gas is used as fuel for vehicles and as a chemical feedstock in the manufacture of plastics and other commercially important organic chemicals. Due to the wide array of compositions of the natural gas and broad applications, analysis of natural gas is required.

Conventionally, natural gas is analyzed using gas chromatographs. However, gas chromatographs tend to be bulky, slow, and require frequent calibrations. Other conventional techniques entail absorption based optical techniques, such as photo acoustic spectroscopy, tunable diode laser spectroscopy, or broadband absorption spectroscopy. Generally, the absorption based optical techniques are imprecise due to spectral interference from different natural gas components. Additionally, the absorption based optical techniques are imprecise due to various inert gases that do not have absorption lines, and therefore such inert gases cannot be detected using the absorption based optical techniques. For example, gases, such as, $H_2$ and $N_2$ cannot be measured using absorption based optical techniques.

Another conventional optical analysis technique that may be used for analysis of natural gas is Raman spectroscopy or Raman scattering. Raman scattering entails irradiation of the atoms and molecules of natural gas by photons (hereinafter referred to as 'incident photons') of a light beam. The irradiation of the atoms and molecules of the natural gas, by the incident photons, in-elastically scatters a very small fraction of the incident photons. The in-elastically scattered incident photons constitute Raman signals. The Raman signals may thus be used for the analysis of the natural gas. However, due to the small fraction of the in-elastically scattered photons, the signal to noise ratio of the Raman signals is very low which may result in imprecise analysis of the natural gas.

Therefore, it would be advantageous to provide improved systems and methods to analyze natural gas with improved precision and speed. Furthermore, it would be desirable to provide novel and compact systems for analyzing natural gas.

BRIEF DESCRIPTION

A system is presented. The system includes an electromagnetic radiation source configured to generate a mode-matched electromagnetic radiation that irradiates a gas-mixture filled in a gas compartment at a determined pressure 'P' bars, an intensity enhancement mechanism that internally reflects the mode-matched electromagnetic radiation a plurality of times to achieve an effective intensity 'E', of reflected electromagnetic radiation in a region of interest, that is 'N' times an intensity of the mode-matched electromagnetic radiation, and a detection subsystem that analyses the gas-mixture based upon Raman scattered photons emitted from the region of interest, wherein a product of the '13' and the 'N' is at least 30.

A system is presented. The system includes an electromagnetic radiation source configured to generate a mode-matched electromagnetic radiation that irradiates a gas-mixture filled in a gas compartment at a determined pressure 'P' bars, an intensity enhancement mechanism that internally reflects the mode-matched electromagnetic radiation a plurality of times, 'N', in a region of interest to achieve an effective intensity 'E', of reflected electromagnetic radiation, that is the 'N' times the intensity of the mode-matched electromagnetic radiation, and a detection subsystem that analyses the gas-mixture based upon Raman scattered photons emitted from the region of interest, wherein a product of the 'P' and the 'N' is at least 30.

A gas-mixture analyzer is presented. The gas analyzer includes an electromagnetic radiation source configured to generate mode-matched electromagnetic radiation that is directed into a gas compartment having a gas-mixture, wherein the gas compartment is substantially at a pressure 'P' bars, an intensity enhancement mechanism within the gas compartment that internally reflects the mode-matched electromagnetic radiation, by passing, overlapping and intersecting a plurality of times through a region of interest to achieve an effective intensity 'E', of reflected electromagnetic radiation in the region of interest, that is 'N' times an intensity of the mode-matched electromagnetic radiation, and a detection subsystem that analyses the gas-mixture based upon Raman scattered photons emitted from the region of interest, wherein a product of the '13' and the 'N' is at least 30.

A method for analyzing a gas-mixture is presented. The method includes the steps of filling a gas-mixture into a gas compartment until it reaches a pressure 'P' bars, internally reflecting mode-matched electromagnetic radiation in an intensity enhancement mechanism by passing, overlapping and intersecting, multiple times in a region of interest to achieve an effective intensity 'E', of reflected electromagnetic radiation in the region of interest, that is 'N' times the intensity of the mode-matched electromagnetic radiation, and controlling the pressure 'P' of the gas-mixture and the number 'N' such that a product of the number 'N' and the pressure 'P' is at least 30; and analyzing the gas-mixture based upon the Raman scattered photons to determine at least one of a concentration of individual gases in the gas-mixture and an energy content of the gas-mixture.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

The present systems and methods, described in detail hereinafter, monitor and analyze a gas-mixture. The gas-mixture, for example, may be natural gas, liquid nitrogen gas, synthetic gas, liquid petroleum gas, process gas, sour gas, sweet gas, or the like. The analysis of a gas-mixture, includes a number of factors, for example: determination of composition of the gas-mixture, determination of concentration of gases in the gas mixture, determination of energy content of the gas-mixture, and determination of British Thermal Units (BTU) of the gas-mixture. The analysis of a gas-mixture may also include other qualitative and quantitative analysis of the gas-mixture. The present novel systems and techniques use Raman scattering to more precisely analyze the gas-mixture. Unlike conventional techniques, the present novel systems and techniques enhances the signal to noise ratio of Raman signals by: using an intensity enhancement mechanism that achieves a desired effective intensity of electromagnetic radiation at a region of interest, and by controlling the pressure of a gas-mixture to analyze the gas-mixture. Therefore, unlike conventional systems, the present novel systems and techniques do not require expensive and bulky electromagnetic radiation sources to analyze a gas-mixture. The present novel systems have a compact size, and therefore are field deployable. The present novel systems and techniques analyze a gas-mixture in real-time, for example in seconds. The present novel systems and methods may analyze a gas-mixture by collecting a sample of the gas-mixture outside the oil well/pipeline/conduit or gas well/pipeline/conduit.

As used herein, the term "mode-matched electromagnetic radiation" refers to an electromagnetic radiation beam that has been adjusted to achieve a diameter and divergence as per the requirements of an intensity enhancement mechanism. The intensity enhancement mechanism, as used herein, refers to optics and optical systems that are used to focus the mode-matched electromagnetic radiation to the region of interest and internally reflect the mode-matched electromagnetic radiation within the gas compartment. As used herein, the term "internally reflects" refers to substantial total reflection of mode-matched electromagnetic radiation inside an intensity enhancement mechanism and a gas compartment, wherein the intensity enhancement mechanism is located inside the gas compartment. For example, a mode-matched electromagnetic radiation is substantially reflected when at least about 90% of the mode-matched electromagnetic radiation is reflected.

As used herein, the term "region of interest" is a portion of the volume of a gas compartment and an intensity enhancement mechanism, wherein the intensity enhancement mechanism internally reflects mode-matched electromagnetic radiation to achieve highest effective intensity, of the reflected mode-matched electromagnetic radiation, in the portion of the volume of the gas compartment and the intensity enhancement mechanism. As used herein, the term "effective intensity" is used to refer to a combined intensity of reflected electromagnetic radiation experienced by a gas-mixture in a region or a subset of the volume of a gas compartment, containing the gas-mixture, and an intensity enhancement mechanism.

Figure 1:
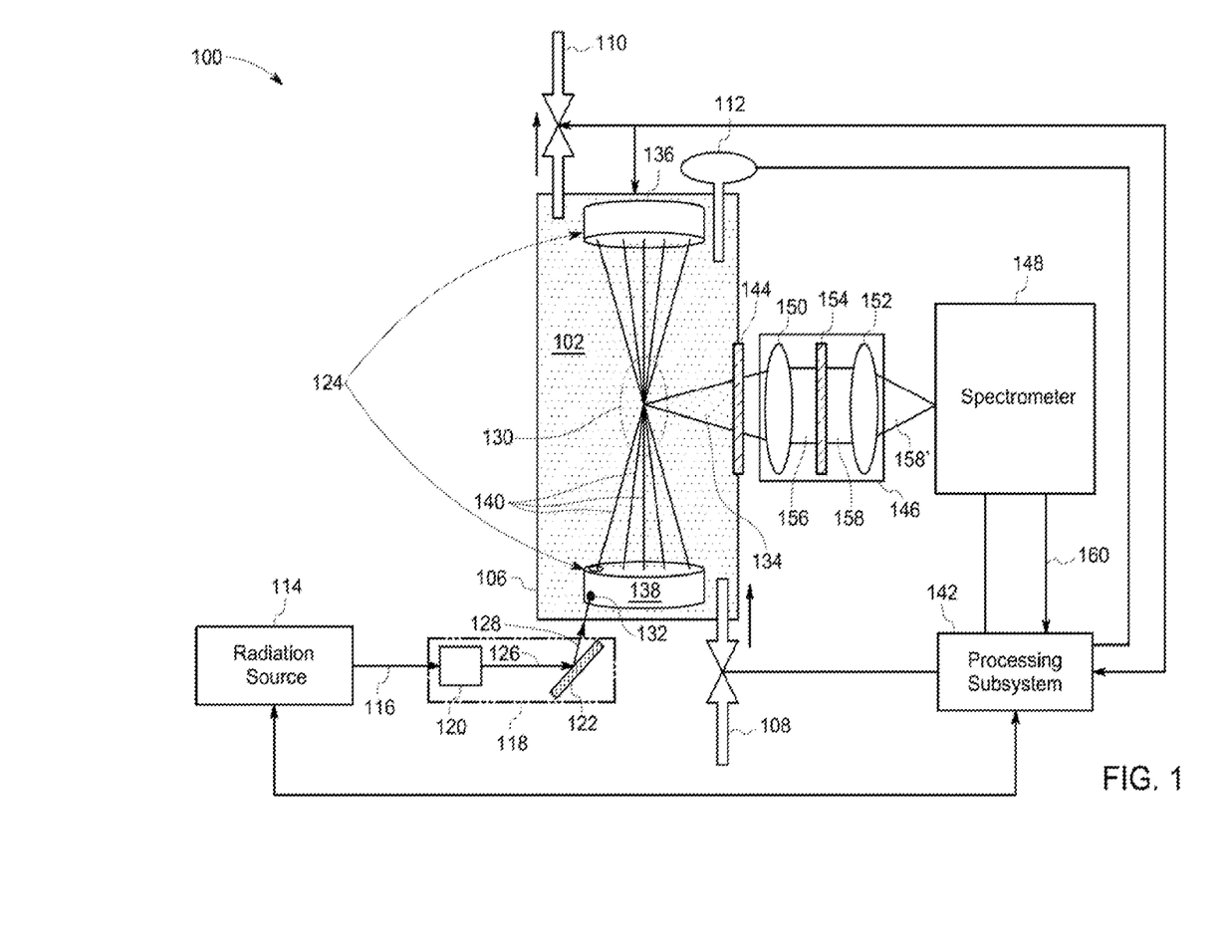
FIG. 1 is a block diagram of a system to analyze a gas-mixture, in accordance with one embodiment of the present systems.

Referring to FIG. 1, a block diagram of a system 100 to analyze a gas-mixture 102, in accordance with certain aspects of the present techniques, is presented. In one embodiment, the gas-mixture 102 is a natural gas. In another embodiment, the gas-mixture 102, for example, may be liquid nitrogen gas, synthetic gas, liquid petroleum gas, process gas, sour gas, sweet gas, or the like. The system 100, for example, applies an optical analysis technique to analyze the gas-mixture 102. Particularly, the system 100 applies Raman Scattering on the gas-mixture 102 to analyze the gas-mixture 102. The gas-mixture 102, for example, is a sample collected from an oil pipeline or a gas pipeline. In one embodiment, the system 100 determines the composition of the gas-mixture 102, and concentration of gases in the gas-mixture 102. In another embodiment, the system 100 determines the energy content of the gas-mixture 102.

As shown in FIG. 1, the system 100 includes a gas compartment 106 containing the gas-mixture 102 at a pressure '13'. The gas compartment 106, for example is made of a material that is opaque or otherwise blocking visible electromagnetic radiation. For example, the gas compartment 106 may be made of stainless steel, Inconel, brass, or another material that is opaque to visible electromagnetic radiation. In the presently contemplated configuration, the gas compartment 106 includes a gas-mixture-inlet-valve 108, a gas-mixture outlet valve 110, and a gauging device 112. The gas-mixture-inlet-valve 108 is used to fill the gas-mixture 102 inside the gas compartment 106. In one embodiment, the gas-mixture-inlet-valve 108 is a pressure regulator that is used to fill and regulate the pressure '13' of the gas-mixture 102. As previously noted, the gas-mixture 102 is filled in the gas compartment 106 until the pressure of the gas-mixture 102 is 'W. In one embodiment, the pressure 13' of the gas-mixture 102 in the gas compartment 106 may be in the range of about 4.5 bars to about 20 bars. In another embodiment, the pressure '13' of the gas-mixture 102 may be in the range of about 4.5 bars to 35 bars when the gas compartment 106 and other parameters are managed, such that the pressure of the gas-mixture 102 is stable and does not show fluctuations. Furthermore, the gas-mixture outlet valve 110 is used to evacuate the gas-mixture 102 from the gas-compartment 106 after the analysis of the gas-mixture 102. The gauging device 112 measures and displays the pressure '13' of the gas-mixture 102 in the gas compartment 106.

The system 100 further includes a radiation source 114. For example, the radiation source 114 may be a coherent source, an incoherent source, a visible light source, an infrared source, or the like. The coherent source in another example is a laser source. The incoherent source may be a Light Emitting Diode (LED). The radiation source 114 generates electromagnetic radiation 116 that is directed towards a mode-matching device 118. The mode-matching device 118, for example, may include a dual mirror telescope, an arrangement of one or more mirrors/lenses, a polarization control optics, or combinations thereof. The radiation source 114 and the mode-matching device 118 may be collectively referred to as an electromagnetic radiation source.

Example of a Mode-matching Device

In the presently contemplated configuration of FIG. 1, the mode-matching device 118 includes polarization control optics 120 and a plane mirror 122. While the presently contemplated configuration includes the plane mirror 122, in certain embodiments the plane mirror 122 may be substituted by one or more lenses, one or more plane mirrors, or combinations thereof. In the embodiment of FIG. 1, the polarization control optics 120 receives the electromagnetic radiation 116 from the radiation source 114. The polarization control optics 120 polarizes the electromagnetic radiation 116 to achieve a desired direction and span of output electromagnetic radiation 134 generated by an intensity enhancement mechanism 124. In the presently contemplated configuration, the polarization control optics 120 polarizes the electromagnetic radiation 116 to generate polarized electromagnetic radiation 126. The polarized electromagnetic radiation 126 is directed onto the plane mirror 122. The plane mirror 122 reflects the polarized electromagnetic radiation 126 to generate mode-matched electromagnetic radiation 128. The plane mirror 122 is placed at a position/location with respect to the position or location of the polarization control optics 120 such that the polarized electromagnetic radiation 126 is reflected at a determined angle of reflection to generate the mode-matched electromagnetic radiation 128. The plane mirror 122 directs the mode-matched electromagnetic radiation 128 into the gas compartment 106 and into the intensity enhancement mechanism 124. Particularly, the reflection of the polarized electromagnetic radiation 126 at the determined angle of reflection directs the mode-matched electromagnetic radiation 128 into the gas compartment 106 and into the intensity enhancement mechanism 124. The determined angle is an angle of reflection of the mode-matched electromagnetic radiation 128 that allows the mode-matched electromagnetic radiation 128 into the gas compartment 106 and into the intensity enhancement mechanism 124, such that, the mode-matched electromagnetic radiation 128 passes through a region of interest 130 in the intensity enhancement mechanism 124. The region of interest 130, for example, may be a concentric point, a confocal region, or a collection of confocal points of the intensity enhancement mechanism 124. The region of interest 130, for example, may have a diameter of about 0.1 mm to about 10 mm.

The mode-matching device 118, for example changes the properties, such as, diameter and divergence of the electromagnetic radiation 116 as per the requirements of the intensity enhancement mechanism 124 to generate the mode-matched electromagnetic radiation 128. For example, the mode-matching device 118 may change the diameter of the electromagnetic radiation 116 to generate the mode-matched electromagnetic radiation 128 that has a diameter different from the diameter of the electromagnetic radiation 116.

As previously noted, the system 100 further includes the intensity enhancement mechanism 124. The intensity enhancement mechanism 124, for example, is an optical cavity, an optical resonator, a confocal resonator, a multipass Raman cell, an off-axis confocal cavity, an integrating sphere, a micro-cavity, or combinations thereof. In the presently contemplated configuration, the intensity enhancement mechanism 124 is a multipass Raman cell. The intensity enhancement mechanism 124 is located inside the gas compartment 106. In the embodiment of FIG. 1, the mode-matched electromagnetic radiation 128 enters via a sapphire entrance window 132 into the intensity enhancement mechanism 124 and the gas compartment 106. In the presently contemplated configuration, the intensity enhancement mechanism 124 includes a first mirror 136 and a second mirror 138 that are placed at a distance from each other, and face each other. When the mode-matched electromagnetic radiation 128 enters the intensity enhancement mechanism 124, the mode-matched electromagnetic radiation 128 passes through the region of interest 130, and hits the first mirror 136. The first mirror 136 reflects the mode-matched electromagnetic radiation 128 to pass through the region of interest 130, and thereafter hits the second mirror 138 and is internally reflected back by the second mirror 138 to again pass through the region of interest 130. In one embodiment, the intensity enhancement mechanism 124 is designed such that the mode-matched electromagnetic radiation 128 is reflected 'N' times within the intensity enhancement mechanism 124. For example, an optical design of the intensity enhancement mechanism 124, and/or a mirror curvature and a mirror diameter of the first mirror 136 and the second mirror 138 may be chosen such that the mode-matched electromagnetic radiation 128 is internally reflected 'N' times through the region of interest 130 and within the intensity enhancement mechanism 124.

Accordingly the mode-matched electromagnetic radiation 128 is internally reflected multiple times by the first mirror 136 and the second mirror 138 resulting in multiple passes, overlaps, and intersection of the mode-matched electromagnetic radiation 128 through the region of interest 130. The multiple internal reflections of the mode-matched electromagnetic radiation 128 shall hereinafter be collectively referred to as "reflected electromagnetic radiation 140". The multiple passes, overlaps, and intersection of the mode-matched electromagnetic radiation 128 in the region of interest 130 results in an effective intensity 'E' of the reflected electromagnetic radiation 140 in the region of interest 130. The effective intensity 'E' of the reflected electromagnetic radiation 140 in the region of interest 130 is the 'N' times the intensity of the mode-matched electromagnetic radiation 128. In one embodiment, the intensity enhancement mechanism 124 internally reflects the mode-matched electromagnetic radiation 128 the 'N' times to achieve the effective intensity 'E', of the reflected electromagnetic radiation 140, that is 'N' times the intensity of the mode-matched electromagnetic radiation 128. In one embodiment, the 'N' is in the range of 6 to 300. Accordingly, the intensity enhancement mechanism 124 substantially internally reflects the mode-matched electromagnetic radiation 128 multiple times to achieve the effective intensity 'E', of the reflected electromagnetic radiation 140 in the region of interest 130. It is noted that an effective intensity of the reflected electromagnetic radiation 140 in another region, having a volume similar to the volume of the region of interest 130, located in the gas compartment 106 and the intensity enhancement mechanism 124 is less than the effective intensity 'E' of the reflected electromagnetic radiation 140 in the region of interest 130. The radiation source 114, the intensity enhancement mechanism 124, and the gas-mixture-inlet-valve 108 are controlled to achieve a product of the 'N' and 'P' at least equal to 30. In one embodiment, the product of the 'N' and the 'P' may be in the range of about 30 to about 6000. In another embodiment, when the gas compartment 106 is designed such that the pressure 'P' of the gas-mixture 102 is stable and does not fluctuate, the product of the 'N' and the 'P' may be in the range of about 30 to about 10,500.

In the presently contemplated configuration, the system 100 further includes a processing subsystem 142 that in one example is operationally coupled to the gas-mixture-inlet-valve 108, the gas-mixture-outlet-valve 110, the radiation source 114, the mode-matching device 118, and the intensity enhancement mechanism 124. The processing subsystem 142 activates the gas-mixture-inlet-valve 108 to fill the gas-mixture 102 into the gas compartment 106 till the pressure of the gas-mixture 102 is 'P'. Furthermore, the processing subsystem 142 controls the radiation source 114 to generate the electromagnetic radiation 116 that enters the mode-matching device 118. Additionally, the processing subsystem 142 controls the mode-matching device 118 to generate the mode-matched electromagnetic radiation 128. Additionally, the processing subsystem 142 controls the intensity enhancement mechanism 124 and the gas-mixture-inlet-valve 108 to achieve the pressure 'P' of the gas-mixture 102 and the effective intensity 'E' of the reflected electromagnetic radiation 140 in the region of interest 130, such that a product of the pressure 'P' and the 'N' is at least 30. The processing system 142, in one example, is one or more processors and can communicate with the various elements by wired or wireless means.

Due to the presence of the gas-mixture 102 and the reflected electromagnetic radiation 140 in the gas compartment 106, Raman scattering and Rayleigh scattering occurs in the gas compartment 106 and the intensity enhancement mechanism 124 generates the output electromagnetic radiation 134. The output electromagnetic radiation 134 comprises Raman scattered photons 158 and Rayleigh scattered photons (not shown). In the presently contemplated configuration, due to the effective intensity 'E' of the reflected electromagnetic radiation 140 in the region of interest 130, a number of the Raman scattered photons 158 emitted from the region of interest 130 is higher than a number of Raman scattered photons emitted from the other regions in the gas compartment 106 and the intensity enhancement mechanism 124. Furthermore, due to the effective intensity 'E,' of the reflected electromagnetic radiation 140 in the region of interest 130 and the pressure 'P' of the gas-mixture 102 in the gas compartment 106, the number of the Raman scattered photons 158 is substantially higher than a number of Raman scattered photons generated using conventional Raman scattering techniques. For example, the number of Raman scattered photons are N*P times higher in comparison to a number of Raman scattered photons emitted using conventional Raman scattering techniques.

The gas compartment 106 comprises a window 144. The size and location of the window 144 is selected, such that, the output electromagnetic radiation 134 substantially emitted from the region of interest 130 substantially passes through the window 144. The output electromagnetic radiation 134 emitted substantially from the region of interest 130 pass through the window 144.

The system 100 further includes collection optics 146 that receive the output electromagnetic radiation 134; blocks the Rayleigh scattered photons and passes through the Raman scattered photons 158 of the output electromagnetic radiation 134. Furthermore, the collection optics 146 collimates and/or decollimates the Raman scattered photons 158 of the output electromagnetic radiation 134 to match the F-number of the Raman scattered photons 158 with the F-number of a spectrometer 148.

Figure 2:
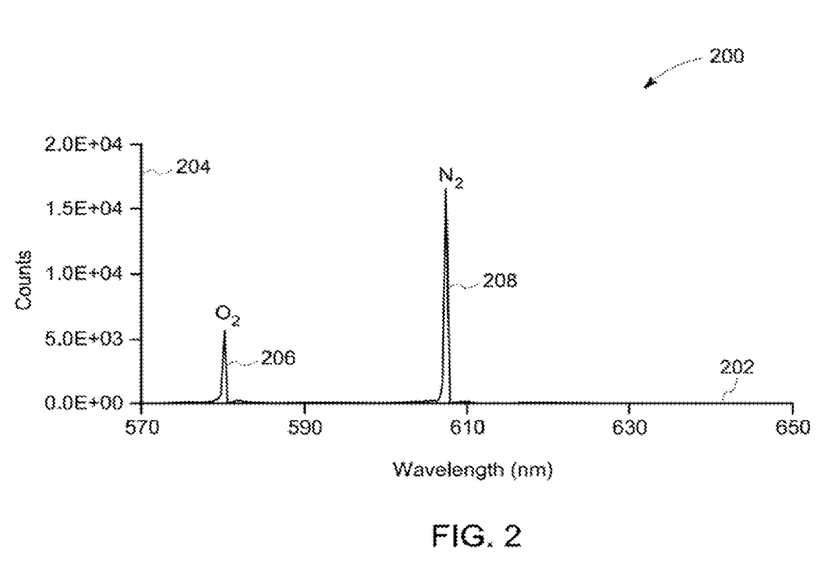
FIG. 2 is an example of a spectrum generated by a spectrometer during the analysis of a gas-mixture.

In the presently contemplated configuration, the collection optics 146 includes a first lens 150, a second lens 152, and a filter 154. In the presently contemplated configuration, the first lens 150 receives the output electromagnetic radiation 134 from the window 144, and collimates the output electromagnetic radiation 134 (hereinafter referred to as "collimated output electromagnetic radiation beam 156) to adjust the diameter of the output electromagnetic radiation beam 134 such that a substantial amount of the collimated output electromagnetic radiation beam 156 passes through the filter 154. Accordingly, the collimated output electromagnetic radiation beam 156 is incident on the filter 154 that blocks Rayleigh scattered photons of the collimated output electromagnetic radiation beam 156 and passes through the Raman scattered photon 158 of the collimated output electromagnetic radiation beam 156. In on embodiment, the filter 154 is a notch filter with a range less than about 5 nm. Thereafter, in the presently contemplated configuration, the Raman scattered photons 158 are transferred through the second lens 152. The second lens 152 focuses the Raman scattered photons 158 (hereinafter referred to as decollimated Raman light beam 158') to match the F-number of the decollimated Raman light beam 158' to the F-number of the spectrometer 148. Furthermore, the second lens 152 directs the decollimated Raman light beam 158' to the spectrometer 148. The decollimated Raman light beam 158' contains light of various wavelengths and frequencies. The spectrometer 148, for example, may be a grating spectrometer, a waveguide spectrometer, or the like. The spectrometer 148 generates a spectrum 160 of gases present in the gas-mixture 102 based upon the decollimated Raman light beam 158' or the Raman scattered photons 158. An example of a spectrum 200 of two gases is shown in FIG. 2. The spectrum 160, for example, is a mapping of different wavelengths of light present in the Raman light beam 158' to the respective intensities of the light present in the Raman light beam 158'. The collection optics 146, the spectrometer 148, and the processing subsystem 142 may be collectively referred to as a detection subsystem.

The spectrometer 148 is operationally coupled to the processing subsystem 142. The processing subsystem 142 receives the spectrum 160 from the spectrometer 148. In one embodiment, the processing subsystem 142 may preprocess the spectrum 160 to remove noise from the spectrum 160. It is noted that due to the usage of the intensity enhancement mechanism 124 that achieves the effective intensity 'E' in the region of interest 130 and the pressure 'P' of the gas-mixture 102 in the gas compartment 106, a signal to noise ratio of the spectrum 160 is substantially higher than a signal to noise ratio of spectrums generated using conventional Raman scattering techniques. The processing subsystem 142 determines the composition, and concentration of gases present in the gas-mixture 102 based upon the spectrum 160. For example, the processing subsystem 142 may compare the spectrum 160 to a reference spectrum to determine the composition of gases present in the gas-mixture 102. The reference spectrum, for example, may be retrieved from a data repository (not shown) by the processing subsystem 142.

As used herein, the term "reference spectrum" is used to refer to mapping of wavelengths of light to corresponding names of gases. The reference spectrum, for example, may include a list of wavelengths and corresponding names of all gases that may be potentially present in the gas-mixture 102 or natural gas. For example, when an excitation laser of 532 nm is used to generate the spectrum 160; and when the processing subsystem 144 compares the spectrum 160 to the reference spectrum, and determines that a light of wavelengths 562 nm to 564 nm, that corresponds to a gas $C_2H_6$, exist in the spectrum 160, then the processing subsystem 142 may determine that the gas $C_2H_6$ exists in the gas-mixture 102. Again, when an excitation laser of 532 nm is used to generate the spectrum 160; and when the processing subsystem 142 determines that a light having a wavelength 571 nm to 573 nm, that corresponds to a gas $CO_2$, exists in the gas-mixture 102, then the processing subsystem 142 may determine that the gas $CO_2$ exists in the gas-mixture 102. Furthermore, the processing subsystem 142 may compare the spectrum 160 to a concentration map of gases to determine concentration of the gases present in the gas-mixture 102. As used herein, the term "concentration map" is used to refer to mapping of concentrations of gases to respective intensity of light or a number of Raman scattered photons, having respective wavelengths, in a spectrum.

Additionally, the processing subsystem 142, in one example, determines BTU of the gas-mixture 102 based upon the concentration, total amount of the gas-mixture, and composition of the gas-mixture 102. The BTU of the gas-mixture 102, for example, may be determined using the following equation (1):

$$\text{Gas} - \text{mixture } BTU = \sum_{k=0}^{n} \text{mole fraction of gas} * \frac{BTU \text{ of gas } k}{\text{unit mole fraction}} \quad (1)$$

An example of a spectrum 200 is shown in FIG. 2. For ease of understanding, FIG. 2 shows the spectrum 200 of two gases including $O_2$ and $N_2$, generated using Raman light beam, such as, the decollimated Raman light beam 158' or the Raman scattered photons 158. The Raman light beam is generated when a gas-mixture, such as, the gas-mixture 102 is irradiated by an excitation laser having a wavelength of 532 nm. The spectrum 200, for example, may be generated by the spectrometer 148 (see FIG. 1). X-axis 202 of the spectrum 200 represents wavelengths of Raman light beam, such as, the decollimated Raman light beam 158'. Y-axis 204 of the spectrum 200 represents intensity/number of Raman scattered photons of the Raman light beam. The spectrum 200 shows two peaks 206, 208. The first peak 206 exists at a wavelength of about 580 nm, and the second peak 208 exists at a wavelength of about 608 nm. When the processing subsystem 142 compares the spectrum 200 to the reference spectrum, and determines that the first peak 206 at the wavelength of about 580 nm corresponds to a gas $O_2$, the processing subsystem 142 may determine that the gas $O_2$ exists in the gas mixture 102. Again, when the processing subsystem 142 compares the spectrum 200 to the reference spectrum, and determines that the second peak 208 at the wavelength of about 607 nm corresponds to the gas $N_2$, then the processing subsystem 142 may determine that the gas $N_2$ exists in the gas-mixture 102. Additionally, the processing subsystem 142 may determine the concentration of the gas $O_2$ and the gas $N_2$ by comparing the intensity of the gas $O_2$ and the gas $N_2$ to the concentration map.

Figure 3:
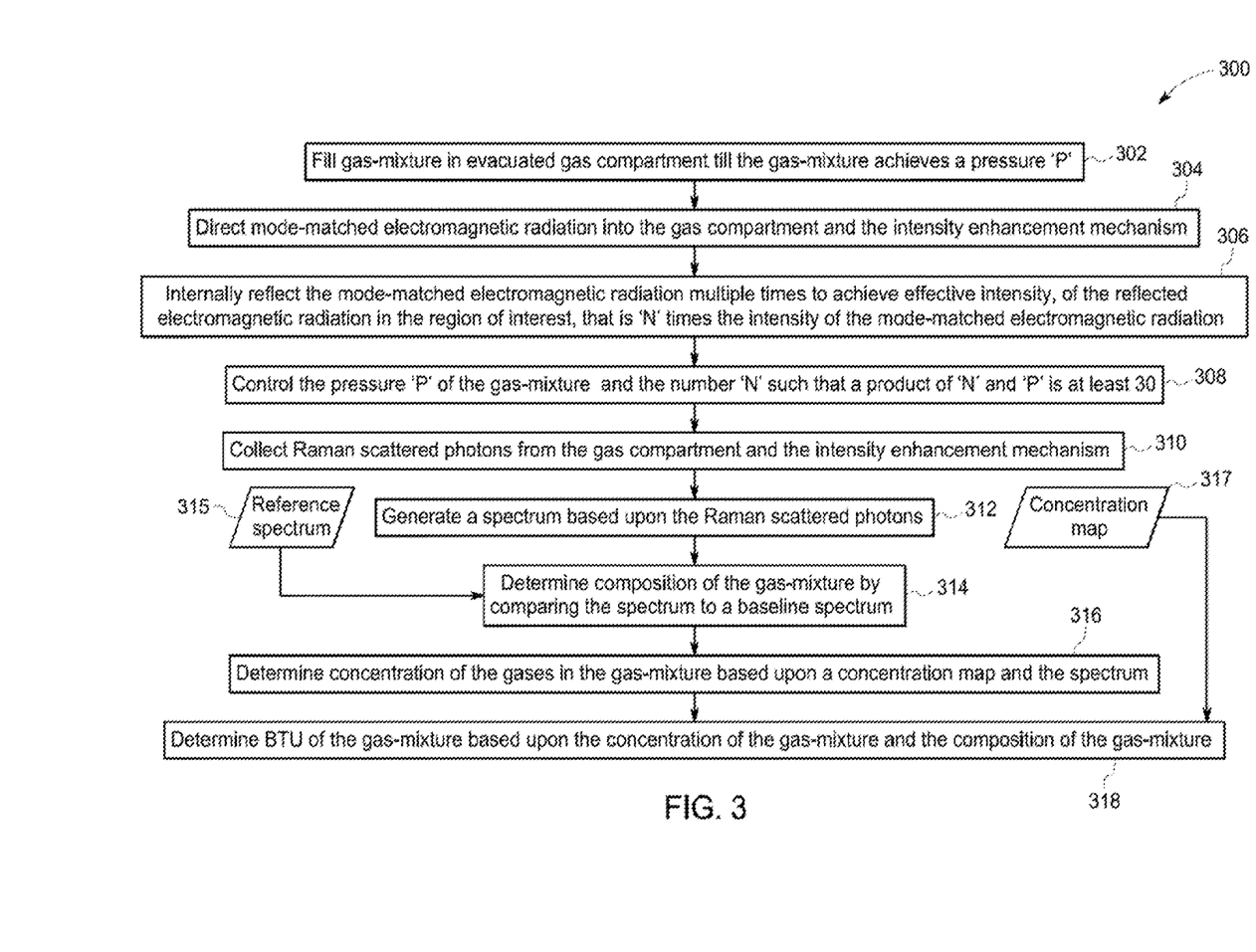
FIG. 3 is a flow chart that illustrates an exemplary method for analysis of a gas-mixture, in accordance with another embodiment of the present techniques.

FIG. 3 is a flow chart 300 that illustrates an exemplary method for analysis of a gas-mixture, in accordance with one embodiment of the present techniques. The gas-mixture, for example, may be natural gas. At block 302, the gas-mixture may be filled into a gas compartment, such as the gas compartment 106 referred to in FIG. 1. The gas-mixture is filled into the gas compartment until the gas-mixture achieves a pressure 'P'. The pressure 'P' of the gas-mixture, for example may be natural gas. The pressure 'P' of the gas-mixture, for example, may be in the range of about 4.5 bars to about 20 bars. In one embodiment, the pressure 'P' of the gas-mixture may be in the range of about 4.5 bars to about 35 bars when the gas compartment 106 is designed such that pressure 'P' of the gas-mixture is stable, and does not fluctuate.

The gas compartment comprises an intensity enhancement mechanism, such as, the intensity enhancement mechanism 124 referred to in FIG. 1. Furthermore, at block 304, mode-matched electromagnetic radiation is directed into the gas compartment and the intensity enhancement mechanism. The mode-matched electromagnetic radiation, for example is the mode-matched electromagnetic radiation 128 referred to in FIG. 1. As previously noted the intensity enhancement mechanism is a device that internally reflects the mode-matched electromagnetic radiation 128. At block 306, the mode-matched electromagnetic radiation is internally reflected by the intensity enhancement mechanism to achieve effective intensity 'E', of the reflected electromagnetic radiation in the region of interest, that is 'N' times the intensity of the mode-matched electromagnetic radiation. At block 308, a processing subsystem, such as, the processing subsystem 142 may control the intensity enhancement mechanism and the gas compartment to adjust the pressure 'P' and the number 'N', such that a product of the pressure 'P' and the number 'N' is at least 30.

Due to the presence of the gas-mixture and the electromagnetic radiation, Raman scattering and Rayleigh scattering occurs in the intensity enhancement mechanism and the gas chamber. Due to the Raman scattering and the Rayleigh scattering, Raman scattered photons and Rayleigh scattered photons are emitted by the reflected electromagnetic radiation. At block 310, Raman scattered photons are collected by a spectrometer. The Raman scattered photons, for example, are the Raman scattered photons 158 or the decollimated Raman light beam 158' referred to in FIG. 1.

At block 312, a spectrum may be generated based upon the Raman scattered photons. The spectrum, for example, may be generated by the spectrometer 148 referred to in FIG. 1. The spectrum, for example, may be similar to the spectrum 160 referred to in FIG. 1, and/or the spectrum 200 referred to in FIG. 2. At block 314, the composition of the gas-mixture may be determined by comparing the spectrum to a reference spectrum 315. Furthermore, at block 316, the concentration of the gases in the gas-mixture may be determined based upon a concentration map 317 and the spectrum. For example, if the spectrum shows that the intensity of a gas $N_2$ in the gas-mixture is 100 counts, and the concentration map indicates that 1 count is equal to 0.01% $N_2$ in a gas-mixture, then it may be determined that the concentration of the gas '$N_2$' is 1. Additionally, at block 318, BTU of the gas-mixture may be determined based upon the concentration of the gases in the gas-mixture, and the composition of the gas-mixture. The BTU, for example, may be determined using the equation (1).

The present novel systems and methods use the intensity enhancement mechanism that enhances the signal to noise ratio of Raman signals generated based upon Raman scattered photons for gases in a gas-mixture, and additionally enhances pressure of the gas-mixture. In other words, the present novel systems and methods increase the number of Raman scattered photons corresponding to gases in a gas-mixture in comparison to conventional Raman scattering techniques. The present novel systems and techniques enhances the signal to noise ratio or the number of Raman scattered photons not only for gases that are present in major amounts but also for gases that are present in minimal amounts in the gas-mixture. Therefore, the present systems and methods simultaneously measure concentrations of multiple gases in gas-mixture, and accurately calculate BTU content and other gas parameters of the gas-mixture.

Figure 4:
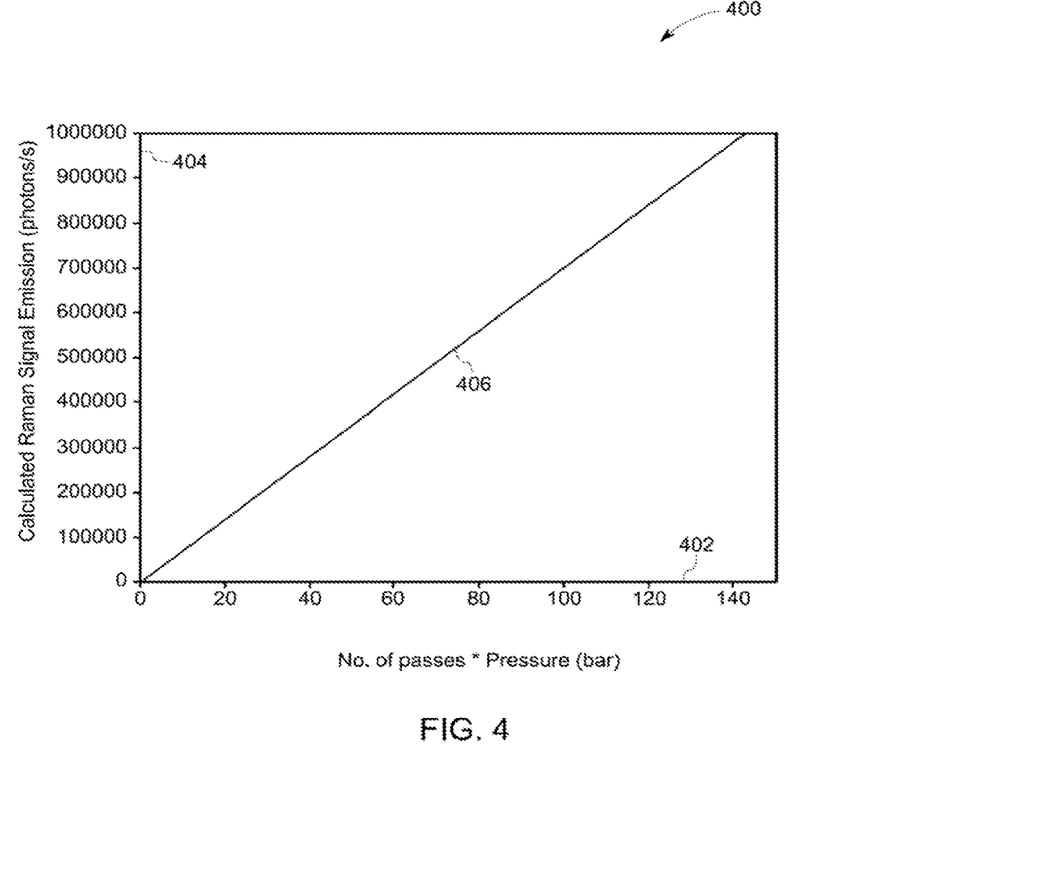
FIG. 4 shows a simulated graph to show an increase in the number of Raman scattered photons corresponding to a gas $N_2$ as a function of a number of passes/reflections in an intensity enhancement mechanism.

FIG. 4 shows a simulated graph 400 to show an increase in the number of Raman scattered photons corresponding to a gas $N_2$ as a function of a number of passes/reflections N in the intensity enhancement mechanism 124 referred to in FIG. 1. A mode-matched electromagnetic radiation of 100 mW having a wavelength of 532 nm is directed into the intensity enhancement mechanism 124 located in the gas compartment 106 referred to in FIG. 1. The gas compartment 106 is filled with the gas-mixture 102. A number of reflections in the intensity enhancement mechanism 124 are gradually increased and a number of Raman scattered photons corresponding to the gas $N_2$ for each change in the number of internal reflections is observed. The observations are shown in the form of the graph 400.

X-axis 402 represents number of a product of number 'N' of internal reflections/passes in the intensity enhancement mechanism 124 and a pressure of the gas-mixture 102. In other words, X-axis 402 represents a product of 'N' and 'P'. Y-axis 404 represents a number of Raman scattered photons corresponding to the gas $N_2$ wherein the concentration of the gas $N_2$ in the gas-mixture 102 is 3%. As shown by a curve 406, the number of Raman scattered photons increases with an increase in the product of the 'N' and 'P'. Accordingly, the present systems and techniques increase the number of Raman scattered photons by controlling a product of 'N' and 'P' to at least 30. Maintaining the product of the 'N' and 'P' as at least 30 ensures that a signal to noise ratio in Raman signals (generated based upon the number of Raman scattered photons) is significantly high to enable precise determination of the presence and concentration of gases in the gas-mixture 102.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A system, comprising:
   an electromagnetic radiation source configured to generate a mode-matched electromagnetic radiation that irradiates a gas-mixture filled in a gas compartment at a determined pressure 'P' of about 4.5 bars to 35 bars;
   an intensity enhancement mechanism that internally reflects the mode-matched electromagnetic radiation a plurality of times to achieve an effective intensity 'E', of reflected electromagnetic radiation in a region of interest, that is 'N' times an intensity of the mode-matched electromagnetic radiation; and
   a detection subsystem that analyses the gas-mixture based upon Raman scattered photons emitted from the region of interest.

2. The system of claim 1, wherein the intensity enhancement mechanism internally reflects the mode-matched electromagnetic radiation to pass, overlap and intersect the mode-matched electromagnetic radiation in the region of interest to achieve the effective intensity 'E' of the reflected electromagnetic radiation in the region of interest.

3. The system of claim 1, wherein the intensity enhancement mechanism is an optical cavity, an optical resonator, a confocal resonator, a multipass Raman cell, an off-axis confocal cavity, an integrating sphere, a micro-cavity, or combinations thereof.

4. The system of claim 1, wherein the electromagnetic radiation source comprises:
   a radiation source that generates electromagnetic radiation; and
   a mode-matching device that mode-matches the electromagnetic radiation as per the requirements of the intensity enhancement mechanism.

5. The system of claim 4, wherein the radiation source is a coherent source, an incoherent source, a visible light source, or an infrared source.

6. The system of claim 1, wherein effective intensity of the reflected electromagnetic radiation in another region, having a volume similar to the volume of the region of interest, and located within the gas compartment and the intensity enhancement mechanism is less than the effective intensity 'E' of the reflected electromagnetic radiation in the region of interest.

7. The system of claim 1, wherein the region of interest is a concentric point, a confocal region, or a collection of confocal points of the intensity enhancement mechanism.

8. The system of claim 1, wherein the intensity enhancement mechanism is located inside the gas compartment.

9. The system of claim 1, wherein the gas-mixture is a sample of natural gas collected from a gas pipeline or an oil pipeline.

10. The system of claim 1, wherein the region of interest has a diameter of about 0.1 mm to about 10 mm.

11. The system of claim 1, wherein a product of the 'N' and the 'P' is in the range of about 30 to about 6000.

12. The system of claim 1, wherein, a product of the 'N' and the 'P' is in the range of about 30 to about 10,500 when the gas compartment is designed such that the pressure 'P' of the gas-mixture is stable, and the pressure does not fluctuate.

13. The system of claim 1, wherein the 'N' is in the range of 6 to 300.

14. The system of claim 1, wherein the detection subsystem comprises:
   a collection optics that adjusts the F-number of the Raman scattered photons and collimates/decollimates the Raman scattered photons as per the requirements of a spectrometer; the spectrometer that generates a spectrum based upon the Raman scattered photons; and
   a processing subsystem that analyses the gas-mixture based upon the Raman scattered photons.

15. The system of claim 1, wherein the detection subsystem analyzes the gas-mixture by:
   generating a spectrum based upon the Raman scattered photons;
   determining composition of the gas-mixture by comparing the spectrum and a reference spectrum stored in a data repository;
   determining concentration of gases present in the gas-mixture based upon a concentration map and the spectrum; and
   determining British Thermal Units of the gas-mixture based upon the concentration and composition of the gas-mixture.

16. The system of claim 1, wherein the gas-mixture comprises natural gas, liquid nitrogen gas, synthetic gas, liquid petroleum gas, process gas, sour gas, or sweet gas.

17. A system, comprising:
   an electromagnetic radiation source configured to generate a mode-matched electromagnetic radiation that irradiates a gas-mixture filled in a gas compartment at a determined pressure 'P' of about 4.5 bars to 35 bars;
   an intensity enhancement mechanism that internally reflects the mode-matched electromagnetic radiation a plurality of times, 'N' in a region of interest to achieve an effective intensity 'E', of reflected electromagnetic radiation, that is the 'N' times the intensity of the mode-matched electromagnetic radiation; and
   a detection subsystem that analyses the gas-mixture based upon Raman scattered photons emitted from the region of interest.

18. A gas-mixture analyzer, comprising:

an electromagnetic radiation source configured to generate mode-matched electromagnetic radiation that is directed into a gas compartment having a gas-mixture, wherein the gas compartment is at a pressure 'P' of about 4.5 bars to 35 bars;

an intensity enhancement mechanism within the gas compartment that internally reflects the mode-matched electromagnetic radiation, by passing, overlapping and intersecting a plurality of times through a region of interest to achieve an effective intensity 'E', of reflected electromagnetic radiation in the region of interest, that is 'N' times an intensity of the mode-matched electromagnetic radiation; and a detection subsystem that analyses the gas-mixture based upon Raman scattered photons emitted from the region of interest.

19. A method for analyzing a gas-mixture, comprising:

filling a gas-mixture into a gas compartment until it reaches a pressure 'P' of about 4.5 bars to 35 bars;

internally reflecting mode-matched electromagnetic radiation in an intensity enhancement mechanism by passing, overlapping and intersecting, multiple times in a region of interest to achieve an effective intensity 'E', of reflected electromagnetic radiation in the region of interest, that is 'N' times the intensity of the mode-matched electromagnetic radiation;

controlling the pressure 'P' of the gas-mixture and the number 'N'; and analyzing the gas-mixture based upon the Raman scattered photons to determine at least one of a concentration of individual gases in the gas mixture and an energy content of the gas mixture.

* * * * *